United States Patent
Czygan et al.

(10) Patent No.: US 8,491,485 B2
(45) Date of Patent: Jul. 23, 2013

(54) ELECTROMEDICAL IMPLANT AND MONITORING SYSTEM INCLUDING THE ELECTROMEDICAL IMPLANT

(75) Inventors: Gerald Czygan, Buckenhof (DE); Michael Lippert, Ansbach (DE); Olaf Skerl, Bad Doberan (DE)

(73) Assignee: Biotronik SE & Co. KG (DE)

( * ) Notice: Subject to any disclaimer, the term of this patent is extended or adjusted under 35 U.S.C. 154(b) by 55 days.

(21) Appl. No.: 13/038,428

(22) Filed: Mar. 2, 2011

(65) Prior Publication Data

US 2011/0224527 A1 Sep. 15, 2011

Related U.S. Application Data

(60) Provisional application No. 61/311,789, filed on Mar. 9, 2010.

(51) Int. Cl.
*A61B 5/024* (2006.01)
*A61B 5/026* (2006.01)

(52) U.S. Cl.
USPC .............................. 600/500; 600/502; 600/505

(58) Field of Classification Search
USPC ................. 600/481, 483, 485, 486, 500, 502, 600/504, 506, 507
See application file for complete search history.

(56) References Cited

U.S. PATENT DOCUMENTS

| | | | |
|---|---|---|---|
| 5,743,856 A | 4/1998 | Oka et al. | |
| 5,857,975 A * | 1/1999 | Golub | 600/485 |
| 6,625,487 B2 * | 9/2003 | Herleikson | 607/8 |
| 6,748,262 B2 | 6/2004 | Harada et al. | |
| 7,029,447 B2 | 4/2006 | Rantala | |
| 8,162,841 B2 * | 4/2012 | Keel et al. | 600/486 |
| 2006/0135886 A1 | 6/2006 | Lippert et al. | |
| 2008/0183083 A1 | 7/2008 | Markowitz | |
| 2009/0062667 A1 | 3/2009 | Fayram et al. | |
| 2010/0022899 A1 | 1/2010 | Kolberg et al. | |
| 2012/0065528 A1 * | 3/2012 | Gill et al. | 600/509 |

FOREIGN PATENT DOCUMENTS

| | | |
|---|---|---|
| DE | 100 61 189 A1 | 6/2002 |
| DE | 10 2005 042041 A1 | 3/2007 |
| EP | 1 665 983 A2 | 6/2006 |
| EP | 2 149 336 A1 | 2/2010 |

* cited by examiner

*Primary Examiner* — Brian T Gedeon
(74) *Attorney, Agent, or Firm* — Craig A. Fieschko, Esq.; DeWitt Ross & Stevens S.C.

(57) ABSTRACT

An electromedical implant (100, 101, 102, 103) for monitoring a cardiac blood flow (B1) of a patient includes a detector (10, 10', 10") which obtains a first measurement signal (S1) associated with the cardiac blood flow (B1) and a second measurement signal (S2) associated with the epithoracic, peripheral blood flow (B2). A monitoring assembly (20) then generates a first parameter (P1) from the first measurement signal (S1) which is indicative of a time ($t_{sys}$) at which blood is ejected from the heart, and a second parameter (2) from the second measurement signal (S2) which is indicative of a time ($t_{gef}$) of a blood pulse in the thoracic tissue which is associated with the ejection of blood. An evaluation unit (30) then generates a pulse transit time ($\Delta t = t_{gef} - t_{sys}$) from the first parameter (P1) and the second parameter (P2). The detector (10, 10', 10") includes an impedance measuring unit (12) having an electrode assembly (11, 11') for detection of at least the second measurement signal (S2) in the form of an impedance signal.

23 Claims, 4 Drawing Sheets

ELECTROMEDICAL IMPLANT AND MONITORING SYSTEM INCLUDING THE ELECTROMEDICAL IMPLANT

CROSS-REFERENCE TO RELATED APPLICATIONS

This application claims priority under 35 USC §119(e) to U.S. Provisional Patent Application 61/311,789 filed Mar. 9, 2010, the entirety of which is incorporated by reference herein.

FIELD OF THE INVENTION

The invention relates to an electromedical implant for monitoring a cardiac blood flow and an epithoracic, peripheral blood flow of a living being. The invention further relates to a monitoring system including the electromedical implant.

BACKGROUND OF THE INVENTION

An electromedical implant of the type mentioned above can be designed and/or used only for monitoring (in which case it is typically referred to as a monitoring implant), or for both monitoring and therapy (in which case it is typically referred to as a therapy implant). Contrary to therapy implants, such as implantable cardiac stimulators or the like, an monitoring implant for monitoring blood flows of a living being (patient) provides no therapy options. A monitoring implant can be useful for patients having no identified need for therapy in order to monitor the patient's blood flows. For example, the conditions for electrotherapy may not (yet) be diagnosed, or the proper type of electrotherapy to be administered may be unknown, until the patient has been monitored for an extended period using a monitoring implant. Monitoring cardiac blood flow and the epithoracic, peripheral blood flow of a living being have proven to be advantageous for determining a pulse transit time, i.e., the time difference between a time at which blood is ejected from the heart of a patient and the time of a blood pulse in the thoracic tissue, wherein the blood pulse in the thoracic tissue is caused by the ejected blood and is delayed from the time of ejection.

A variety of approaches are known for determining the pulse transit time. For example, U.S. Pat. No. 7,029,447 discloses a non-invasive system for measuring the blood pressure of a patient, wherein the pulse transit time is determined from the difference between the times of the heart ejection event and the arrival of the pulse wave in the periphery of the body using an external measuring device. The time of the cardiac contraction is determined from the externally measured thoracic impedance and the QRS complex of a surface ECG. The arrival of the pulse wave at a peripheral organ, specifically the lower arm, is determined by use of optical plethysmography. U.S. Pat. Nos. 6,748,262 and 5,743,856 describe further non-invasive methods for determining the pulse transit time based on an ECG signal and a thoracic impedance signal.

While such non-invasive systems have proven useful for monitoring purposes, they are disadvantageous and at times cumbersome. However, cardiac invasive systems are generally not a suitable option for patients having no therapy indication, i.e., no (presently) defined need for therapy. The implantation of probes in the heart, for example for determining an ECG signal using a cardiac stimulator, is complex and associated with risks for the patient. In this respect, obtaining thoracic impedance measurements via the probes of a cardiac stimulator, which can be implanted in the heart to obtain an impedance cardiogram (ICG) or electrocardiogram (ECG), is only appropriate for patients suffering from cardiac insufficiency. However, this is unsuitable for patients without an electrotherapy indication. At the same time, this group of patients constitutes a significant portion of patients suffering from cardiac insufficiency.

It would be useful to have an electromedical implant for monitoring a cardiac blood flow and an epithoracic, peripheral blood flow of a living being (patient), which can also be used to monitor a pulse transit time in the long term, without requiring cardiac invasion. In this respect, US 2009/0062667 A1 determines a pulse transit time from the peak pulse arrival times of two signals for monitoring arterial blood pressure. Using subcutaneously implanted electrodes, a first signal in the form of an electrocardiogram is determined, which is indicative of an electrical activity of a patient's heart (i.e., the blood ejected from the heart). In addition, a photoplethysmography sensor implanted in the pectoral region is used to obtain a corresponding signal which is indicative of a mechanical activity of a patient's heart (i.e., the arrival of a blood pulse in the pectoral region). This concept can be implemented as an implantable monitor having no electrotherapy device. The electrocardiogram and the photoplethysmography signal are used within an evaluation unit in order to determine an arterial blood pressure.

While measuring electric activity and mechanical activity of a patient's heart is, in principle, helpful for determining a pulse transit time in a monitoring implant, this approach is in need of improvement.

SUMMARY OF THE PREFERRED VERSIONS OF THE INVENTION

The invention involves an electromedical implant, particularly a pure monitoring implant, for monitoring a cardiac blood flow and an epithoracic peripheral blood flow of a living being, by which a measurement signal associated with the epithoracic peripheral blood flow can be determined in a comparatively simple and yet reliable manner. The invention also involves a monitoring system utilizing the electromedical implant, by which the pulse transit time, and preferably additional patient values derived from the pulse transit time, can be monitored and retrieved either briefly or over an extended period.

A preferred version of the electromedical implant includes the following:
- a detector (10, 10', 10") for capturing a first measurement signal (S1) associated with the cardiac blood flow (B1) and a second measurement signal (S2) associated with the epithoracic, peripheral blood flow (B2);
- a monitoring assembly (20) which is connected to the detector (10, 10', 10") and which is equipped to generate:
    from the first measurement signal (S1), a first parameter (P1) which is indicative of a time ($t_{sys}$) at which blood is ejected from the heart, and
    from the second measurement signal (S2), a second parameter (2) which is indicative of a time ($t_{gef}$) of a blood pulse in the thoracic tissue which is associated with the ejection of blood;
- an evaluation unit (30), which is connected to the monitoring assembly (20) and equipped to generate a pulse transit time ($\Delta t$) from the first parameter (P1) and the second parameter (P2);

wherein the detector (10, 10', 10") includes an impedance measuring unit (12) having an electrode assembly (11, 11'), which are equipped to detect at least the second measurement signal (S2) in the form of an impedance signal (S).

The invention also encompasses a monitoring system including the electromedical implant and the aforementioned communication module, wherein the monitoring system further includes a receiving unit for receiving the pulse transit time and/or the evaluation result (preferably wirelessly, with the receiving unit being remote from the implant), and a memory unit (preferably associated with the receiving unit) for storing the pulse transit time and/or the evaluation result.

The term "impedance signal" will be used to refer to a signal resulting from a voltage sampling having a known current emission, or a signal resulting from a current sampling having a known voltage emission, or a similar signal from which the impedance between two poles of the electrode assembly can be deduced. This applies in particular to the impedance at a defined frequency of an electric current or an electric voltage. The impedance can also be determined from a pulse-shaped alternating current or a pulse-shaped alternating voltage.

The term "parameter" shall be understood to refer to any quantifiable characteristic of a measurement signal. As an example, a parameter is indicative of a time when it defines a characteristic of the measurement signal which can be sufficiently defined in terms of time. In principle, the parameter can be generated directly from the measurement signal, or from a signal obtained from the measurement signal, such as by filtration or mathematical derivation or the like. A measurement signal derived directly or indirectly from a signal obtained on the basis of an impedance measurement can be regarded as an impedance signal.

As noted above, a preferred implant generates a first parameter from a first measurement signal associated with the cardiac blood flow that is indicative of a time $t_{sys}$ at which blood is ejected from the heart. The first measurement signal can be advantageously implemented as an electric measurement signal, such as an epithoracic electrocardiogram. A second parameter is generated from a second electric measurement signal, and is indicative of the time $t_{gef}$ of a blood pulse in the thoracic tissue. At least the second measurement signal is preferably detected in the form of an impedance signal.

In a particularly preferred version, the electromedical implant is implemented purely as a monitoring implant (i.e., without a therapy option). The monitoring implant can advantageously be implanted subcutaneously or submuscularly and does not require intracardiac electrodes for monitoring the pulse transit time (though use of such electrodes is possible). The electromedical implant allows capture of a measurement signal associated with the cardiac blood flow, and of a measurement signal associated with the epithoracic, peripheral blood flow, in a particularly simple and reliable manner. The implant is compact and easy to implement.

In the monitoring assembly, a second parameter can be generated from an impedance signal, which is indicative of a time of the blood pulse in the thoracic tissue associated with the blood ejection (which is represented by the first parameter). The first parameter can be generated from an impedance signal which is indicative of the blood ejection. The first measurement signal associated with the cardiac blood flow can also be provided in a variety of other ways, and can be processed in a variety of ways to obtain the first parameter.

The evaluation unit is designed to carry out methods for determining the pulse transit time from the first and second parameters, and thus from the time difference between the time at which blood is ejected from the heart and the time of the blood pulse in the thoracic tissue associated with the blood ejection. The evaluation unit can be employed to obtain information about a vascular state and/or a blood pressure of the living being.

The impedance measuring unit, the monitoring assembly, and the evaluation unit may be provided as part of an electronic circuit provided in a housing of the implant, and which (at least for picking up the second measurement signal) is electrically connected to the electrode assembly. The electrode assembly can advantageously be attached to the housing either directly or by way of a header. The housing preferably includes a battery. In a particularly preferred version, the implant includes a communication module for the wireless transmission of the pulse transit time and/or an evaluation result produced by the evaluation unit on the basis of the pulse transit time. The communication module can preferably be provided in the housing as a telemetry module. A telemetric connection of the electromedical implant to the monitoring system via the communication module enables automatic remote monitoring of a patient by way of the electromedical implant. The patient can thus be monitored remotely by the physician or a service center, and alarm conditions can be generated based on the transmitted pulse transit time and/or evaluation signals, which are displayed in the service center and/or directly at the physician's practice. In this way, a physician can be notified of critical conditions of a patient via the service center, either directly or by way of further communication means, such as an Internet platform, SMS, e-mail, fax or the like. A monitoring system can make patient conditions reported by the electromedical implant available for visualization.

A reduced pulse transit time, for example, can indicate reduced vascular elasticity. Associated therewith is low blood flow of the coronary vessels and an increased risk of cardiac infarction. Low vascular elasticity promotes the deterioration of health in the case of chronic cardiac insufficiency. Vascular elasticity also influences the treatment possibilities for hypertension. Knowledge of the vascular elasticity and the changes thereof can optimize the type and dosage of drugs.

The pulse transit time can also be used to estimate the arterial blood pressure, or changes in blood pressure, provided it is known over a sufficient period of time. Blood pressure is an important systematic variable. Changes in the mean blood pressure, changes in the stress-dependent rise in blood pressure, or blood pressure fluctuations, can be important indications of the development of chronic diseases, such as arterial hypertension or cardiac insufficiency. Such evaluation results and others can advantageously be obtained from the pulse transit time.

The evaluation result preferably includes a parameter indicative of the blood vessel state and/or a parameter indicative of the blood pressure, which can be determined from the pulse transit time. In addition, the evaluation result may include additional parameters which are indicative of a condition of the living being (patient) and which, in principle, can be determined on the basis of the pulse transit time using suitable means and algorithms. The pulse transit time and/or the evaluation results are made available for further use by the memory unit, which can be provided in the implant or the receiving unit. In this way, the pulse transit time and/or the evaluation results can be saved in the form of trends and statistics, such as histograms, and can be queried by the physician during a follow-up examination using a suitable interrogation device. However, a query can also be conducted directly by the patient, or by an authorized service center.

The invention can allow the pulse transit time monitored by the implant, and the parameters included in the evaluation result determined therefrom, to be made available for further analysis. For this purpose, suitable further processing units, or interrogation units, can be provided as part of the monitoring system, which preferably are able to communicate in a wireless manner with the monitoring system and/or the implant, in particular with the receiving unit, and/or are able to access the memory unit.

The invention also encompasses a method for monitoring a cardiac blood flow and an epithoracic peripheral blood flow of a living being, using an electromedical epithoracically implantable implant, wherein the method includes the following steps:

capturing a first measurement signal associated with the cardiac blood flow and a second measurement signal associated with the epithoracic peripheral blood flow;

generating, from the first measurement signal, a first parameter which is indicative of a time $t_{sys}$ at which blood is ejected from the heart, and generating, from the second measurement signal, a second parameter which is indicative of a time $t_{gef}$ of a blood pulse in the thoracic tissue associated with the blood ejection;

generating a pulse transit time $\Delta t$ from the first parameter and the second parameter, wherein the second measurement signal is detected in the form of an impedance signal.

Advantageously, a trigger unit can be provided in the monitoring system for the time-triggered activation of the communication module, for example automatically, in an event-controlled manner, or in a patient- or physician-controlled manner. This can ensure, continuous or as-needed availability of the pulse transit time and/or of the evaluation signal for further processing or analysis.

Advantageously, a processing unit is provided in the monitoring system for processing or converting the data format encoding the pulse transit time and/or the evaluation result. The evaluation result allows construction of a parameter which is indicative, for example, of a critical condition of a patient. A visual representation of the evaluation result could, for example, visualize a critical parameter in a particularly well-organized manner, such as in a histogram or in a color illustration.

The monitoring system furthermore advantageously includes an interrogation unit for querying at least the pulse transit time and/or the evaluation signal by the electromedical implant and/or memory unit. The interrogation unit can be provided as part of a service center, or a patient device, or a physician device. All those involved can directly participate in the communication with the monitoring system and/or the implant. The receiving unit can also be directly associated with a physician, or a patient, or a service enter.

The electrode assembly preferably forms several poles, whereby several impedance signals can be detected using the impedance measuring unit. A pole may be associated with an electrode of the electrode assembly, with the electrode including an electrode body for implementing the pole. Thus, for example, when a two-pole measurement for an impedance signal is made, voltage sampling can be implemented using the same electrodes which are used to express the current. In a three-pole measurement, it is also possible for an impedance signal to carry out a voltage sampling using a first electrode, which is used to express a current, and also using a second available electrode. In a four-pole measurement, for an impedance signal a voltage sampling can be carried out using at least two available electrodes which are not used for emitting current. In principle, several electrodes of the electrode assembly can be associated with several poles, which is advantageous for a preferred measurement configuration.

Different measurement configurations can also be provided in any arbitrary combination simultaneously or alternately. In this way, advantageously several impedance signals having different information contents can be provided at least for the second measurement signal.

In a preferred version of the invention, the impedance measuring unit and the electrode assembly are equipped to detect the first measurement signal in the form of an impedance signal. Preferably, the first and second measurement signals are both impedance signals obtained using a single electrode assembly. A useful arrangement involves equipping the electrode assembly with at least one electrode which is situated relatively close to the implant. An electrode situated close to the implant can be configured separately from the housing, directly on the housing, or directly by the housing of the implant. Electrodes located close to the implant primarily capture effects in the direct vicinity of the implant. The second measurement (impedance) signal is preferably obtained using one or more electrodes of this type. The electrode assembly may also include at least one additional electrode situated further away from the implant than the closely-located electrode, with such electrodes being useful for capturing effects at a larger distance from the implant. One or more electrodes of this type are preferably used to detect the first (impedance) measurement signal.

Advantageously, the impedance measuring unit includes an exciter module for delivering an electric current via the electrode assembly and a sampling module for receiving a voltage via the electrode assembly. Conversely, the exciter module can also be used for delivering a voltage via the electrode assembly and the sampling module can be used for receiving a current via the electrode assembly. An exciter module and sampling module can be implemented in a common module, hereinafter also referred to as a frequency module.

A preferred approach involves obtaining the second measurement signal as an impedance generated as a response to current or voltage delivered at a second excitation frequency by the exciter module. Additionally or alternatively, the first measurement signal can be an impedance signal generated as a response to current or voltage delivered at a first excitation frequency by the aforementioned exciter module, or by a different one. The first measurement signal and the second measurement signal can be different portions of a single impedance signal, and can be separated/sorted from the single impedance signal in accordance with their frequencies, for example by employing a frequency filter to obtain the different signals at different frequencies (or frequency ranges).

It is preferred that the second excitation frequency for the second measurement signal be lower than the first excitation frequency for the first measurement signal. A comparatively high excitation frequency results in a temporal impedance curve which captures the volume change of the heart particularly well, and thus after suitable high-pass frequency filtration, the resulting high-frequency impedance curve is particularly useful for determining the time at which blood is ejected from the heart, i.e., the time $t_{sys}$ at which a ventricular contraction starts. A comparatively low excitation frequency results in a temporal impedance curve which captures the blood flow of the tissue surrounding the implant particularly well, and thus after suitable low-pass frequency filtration, the resulting low-frequency impedance curve is particularly useful for determining the time $t_{gef}$ of arrival of a blood pressure wave in a thoracic vessel.

A preferred approach is to form the second (impedance) measurement signal using an electrode close to the implant of the electrode array and using a second excitation frequency, and to form the first (impedance) measurement signal using an electrode spaced away from the implant of the electrode assembly and using a first excitation frequency higher than the second excitation frequency.

The detector unit can include a clock pulse module which is designed to sequence and/or alternate the second measurement signal and the first measurement signal over time. An impedance signal associated with the second measurement signal can therefore be detected temporally after or before an impedance signal associated with the first measurement signal. The first and second measurement signals can each be repeated multiple times before alternating. These arrangements are usefully implemented by use of a multiplexer or the like.

The detector unit preferably implements the aforementioned arrangements using a frequency module and/or a detector. In a particularly preferred version, the frequency module determines a background signal in the form of a high-frequency impedance measurement signal, in particular at a frequency above the first and/or second excitation frequencies mentioned above. Changing the frequency for an impedance measurement has been found to result in a changed contrast between the blood and tissue (skin and muscles). It was found that blood has higher conductivity than tissue, and that this discrepancy decreases as the frequency increases, and thus a higher contrast exists between blood and tissue at lower frequencies than at high frequencies. As a result, higher frequencies tend to be more greatly influenced by geometric changes, and the differences between lower and higher frequency measurements can be used to isolate and suppress geometric changes in the first and/or second measurement signals.

One version of the invention defines the second measurement signal as a partial segment of a transient impedance measurement signal, wherein the second measurement signal is isolated from the remainder of the impedance measurement signal by an amplitude threshold. The first measurement signal can similarly be defined by a partial segment of a transient impedance measurement signal situated above or below an amplitude threshold. The time of a blood ejection (of the systole) $t_{sys}$ can then be determined from the first measurement signal using a suitable algorithm, and the time $t_{gef}$ of a blood pulse in the thoracic tissue can be determined using a different appropriately suited algorithm.

The electrode assembly may include an electrode which is situated symmetrically around a housing container of the implant. The electrode may be situated on several sides, or all sides, or in an annular or circumferential fashion around a housing container of the implant. By using an electrode situated around a housing container of the implant, the electrode assembly can be designed such that at least the second (impedance) measurement signal can be determined independently of the angular position of the implant in the body tissue. The housing container (or portions thereof) may define one or more electrodes.

The detector for capturing the first measurement signal may include an ECG measuring unit having an electrode assembly, and may detect the first measurement signal in the form of an electrocardiogram (ECG) signal. This form of the first measurement signal has proven to be particularly reliable.

In addition to, or as an alternative to defining the first measurement signal as an impedance signal, further detectors may be provided to detect the first measurement signal. The use of an impedance sensor for detecting the first measurement signal is particularly useful for determining the time at which the blood is ejected from the ventricle. Alternatively or additionally, an acoustic sensor can be used to detect cardiac sounds, thereby allowing cardiac valve closing times to be determined. As another option, an acceleration sensor can be used to directly detect a blood ejection.

Preferably, the detector for capturing the second measurement signal includes one or more detectors, which are selected from the group consisting of acoustic detectors, optical detectors, pressure and/or expansion detectors, and acceleration detectors. These and other detectors can be used in addition to the electrode assembly and the impedance measuring unit for detecting the second measurement signal. As an example, an acoustic detector can be used to detect the flow noise of an epithoracic peripheral blood flow in the vessel; an optical detector can be used to detect a plethysmogram for the blood flow; a mechanical expansion or compression sensor, or another pressure sensor, can be used for capturing a volume pulse in adjoining blood vessels (i.e., an epithoracic peripheral blood flow); and an acceleration detector can detect the movement of the housing, or of a detector connected via a cable, caused by a volume pulse. An acoustic detector, in particular an ultrasound acoustic detector, can be designed to detect the blood flow rate of an epithoracic peripheral blood flow in the area surrounding the implant. A high-frequency detector can be used to detect the change in dielectric properties of a tissue surrounding the implant by way of the pulse wave in the epithoracic peripheral blood flow. All of the foregoing detectors are suitable for generation of a second measurement signal—using impedance and/or one or more other properties—associated with the epithoracic peripheral blood flow, with this signal being used to generate a second parameter which is indicative of a time $t_{gef}$ of a blood pulse in the thoracic tissue and which is associated with blood ejection. In similar respects, one or more of the foregoing detectors can be used to generate the first measurement signal (or an additional first measurement signal) from which a first parameter can be produced, which is indicative of a time $t_{sys}$ at which blood is ejected from the heart.

BRIEF DESCRIPTION OF THE DRAWINGS

Further advantages, characteristics, and details of the invention will be apparent from the description of the exemplary versions of the invention below, and also from the drawings, wherein.

DETAILED DESCRIPTION OF PREFERRED VERSIONS OF THE INVENTION

Figure 1:
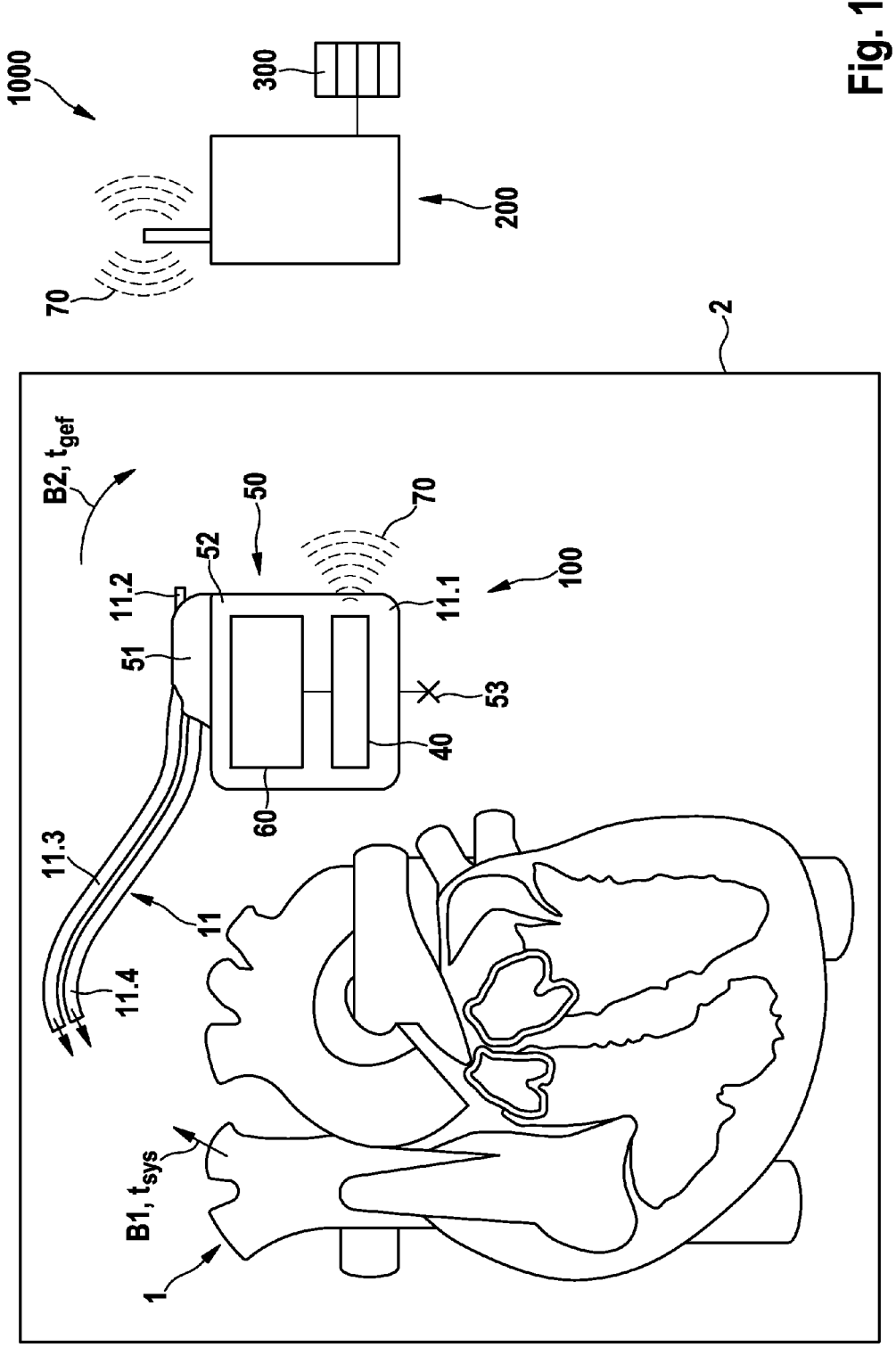
FIG. 1 is a schematic view of a monitoring system exemplifying the invention.

FIG. 1 schematically illustrates an exemplary preferred version of a monitoring system 1000 including an electromedical implant 100, which is equipped to monitor a cardiac blood flow B1 (conceptually illustrated by an arrow), and an epithoracic peripheral blood flow B2 of a living being (also conceptually illustrated by an arrow), the living being preferably being a patient who may or may not have a diagnosis of cardiac insufficiency. Also conceptually illustrated are the heart 1 and the thorax 2 of the patient (the thorax being represented by the box 2 about the heart 1 and the implant 100), with the blood flows B1 and B2 being shown within the thorax 2. The implant 100 is preferably designed purely as a monitoring implant, in other words, it does not perform therapy. The implant 100 includes a housing 50 having a housing container 52, a header 51, and an electrode assembly 11 connected to the housing 50. The implant 100 is situated in the thorax 2 of the patient, subcutaneously in the patient's tissue. To stabilize the position of the implant 100, and deter migration of the implant (and associated uninterpretable movement-related data resulting from the monitoring signals), an anchoring means 53 is preferably provided on the housing 50 of the implant for anchoring the implant 100 in the patient's tissue. Such an anchoring means can be provided, for example, as a sew-in lug, a screw, or other anchoring structure. The anchoring means 53 is preferably designed so that it can also be easily detached from the tissue of the patient, thereby allowing the implant 100 to be removed from the thorax 2 of the patient, if needed.

The electrodes of the electrode assembly 11 preferably include a first electrode 11.1 formed by the housing container 52, a second electrode 11.2 situated at the header 51, and two electrodes 11.3/11.4 connected by leads. An electronic system 60 having a communication module 40 connected thereto is situated in the housing container 52. The electronic system 60, which is preferably provided as a measuring and control electronic system, includes a detector 10, a monitoring assembly 20, and an evaluation unit 30, illustrated in FIG. 2 and explained below. The communication module 40 has an antenna or similar telemetry unit for establishing a wireless telemetry connection 70 to a receiving unit 200 situated outside of the patient. The receiving unit 200 is part of the monitoring system 1000 and allows remote patient monitoring by a physician or a service center. Furthermore, the monitoring system 1000 includes a memory unit 300 connected to the receiving unit 200 by a wired or wireless interface and which is able to store signals transmitted by the implant 100. Such signals include a pulse transit time Δt derived from the monitoring of the cardiac blood flow B1 and the epithoracic peripheral blood flow B2. Owing to the availability of the pulse transit time Δt in the monitoring system 1000 (e.g., in the memory unit 300), evaluation results formed on the basis of the pulse transit time, and patient values and/or patient conditions derived therefrom (in particular critical conditions of the patient), can be made available to a physician, the patient, or a service center. An Internet or other platform (including mobile communication systems, such as for transmitting SMS, e-mail, fax, or the like) can be used to communicate such data from the monitoring system 1000 to other recipients as well. This allows generation of alarm conditions at a location which is external to, and possibly remote from, the implant, based on signal contents transmitted by the implant 100. The patient can thereby receive aid or countermeasures as soon as a critical condition is signaled.

The following description of FIGS. 2-6 explains preferred versions and functions of the implant 100. For sake of clarity and simplicity, identical or similar parts, or parts having identical or similar functions, are denoted with the same reference numerals.

Figure 2:
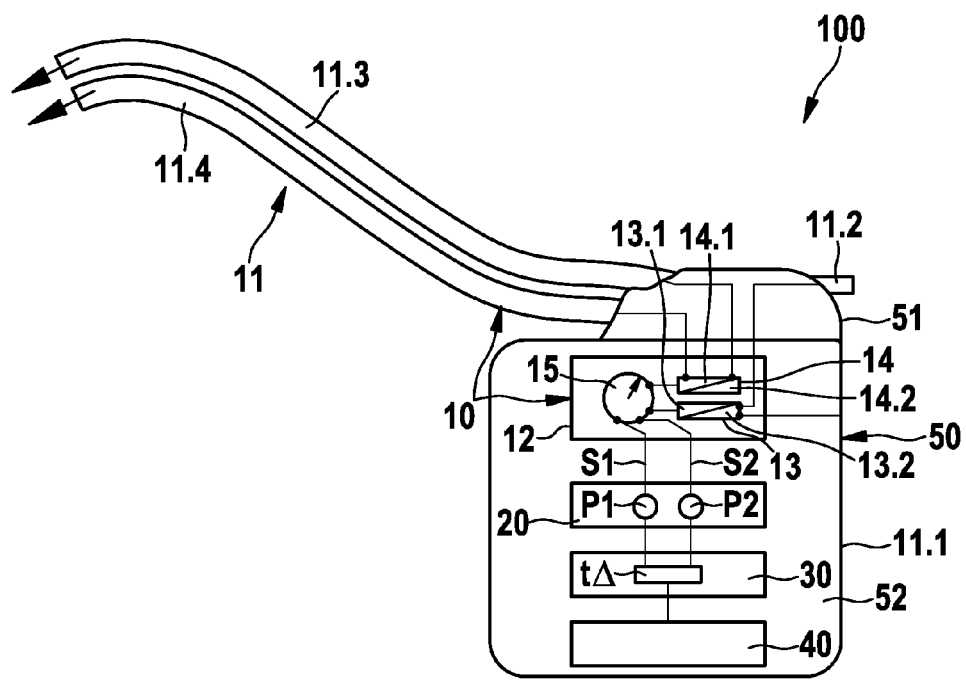
FIG. 2 is a schematic view of an exemplary monitoring implant for monitoring a cardiac blood flow and an epithoracic peripheral blood flow of a living being for use in the monitoring system of FIG. 1.

FIG. 2 shows an enlarged schematic view of the electromedical implant 100 of the monitoring system 1000 of FIG. 1. The implant 100 includes a detector 10 for capturing a first measurement signal S1 associated with the cardiac blood flow B1, and for capturing a second measurement signal S2 associated with the epithoracic peripheral blood flow B2. This detector 10 includes the electrodes 11.1, 11.2, 11.3, 11.4 of the electrode assembly 11 (explained above with reference to FIG. 1), and an impedance measuring unit 12. The electronic system 60 for measuring and control, described above with reference to FIG. 1, includes the impedance measuring unit 12, the monitoring assembly 20 (which is connected to the detector 10), and the evaluation unit 30. The monitoring assembly 20 is configured to generate a first parameter P1 from the first measurement signal S1 which is representative of a time $t_{sys}$ at which blood is ejected from the heart. The monitoring assembly 20 is also configured to produce a second parameter P2 from the second measurement signal S2 which is representative of a time $t_{gef}$ of a blood pulse in the thoracic tissue. This can be done by known signal analysis methods. The blood pulse in the thoracic tissue can thus be determined by monitoring the epithoracic peripheral blood flow B2, wherein the blood pulse in the thoracic tissue is associated with the blood ejection from the heart (as determined by monitoring the cardiac blood flow B1).

An evaluation unit 30 connected to the monitoring assembly 20 is equipped to generate a pulse transit time from the first parameter P1 and the second parameter P2. In the present example, this is by deriving the time $t_{sys}$ (at which blood is ejected from the heart) from the first parameter P1, and deriving the time of the blood pulse in the thoracic tissue from the second parameter P2. This can be done by known signal evaluation algorithms. In the present example, a time difference, which is referred to as the pulse transit time Δt, is obtained by subtracting $t_{gef}$ and $t_{sys}$ from each other ($\Delta t = t_{gef} - t_{sys}$). The evaluation unit 30 converts the parameters P1, P2 into the times $t_{gef}$, $t_{sys}$ and performs the subtraction for Δt. (Further evaluation results can also be determined by the evaluation unit 30 from the pulse transit time, but are not reviewed here.) The pulse transit time Δt is forwarded to the communication module 40, and then transmitted to the receiving unit 200 of the monitoring system 1000 via the telemetry connection 70, where it can be stored and made available in the memory unit 300. The pulse transit time Δt is therefore available to the monitoring system 1000 and can be further processed therein (e.g., in a built-in or external processor), to obtain further evaluation results and patient values which are indicative of a patient condition. Such evaluation results and patient values can advantageously also be visually depicted, for example as histograms, plots of transient signals, or symbolically or numerically depicted mean values, to communicate critical conditions of the patient to a physician or service center in an intuitive and rapidly understandable manner. Thus, alarm conditions can be made available to a physician, the patient, and/or the service center by accessing the monitoring system 1000 and its memory 300.

The monitoring system 1000 can be used for a so-called home monitoring application. For example, the pulse transit time Δt and/or measurement data and other evaluation results based on the pulse transit time Δt can be stored in the memory unit 300 of the monitoring system 1000, and/or within the implant 100 itself, for later access by a physician, service center, or patient. Again, this data can be provided in the form of visually depicted trends, statistics and the like, and/or can be queried and searched. For example, a physician, a service center, or patient, can issue a query via an interrogation device (which may include the receiving unit 200), and a follow-up examination of the patient can be scheduled if appropriate.

In addition, evaluation results and/or the pulse transit time Δt can be regularly transmitted to the receiving unit 200 (which again may be provided as part of a patient, physician, or service center device), such as once a day, and from there they can be forwarded to other recipients via a suitable wired or wireless data connection of the monitoring system 1000. Such data transmission can be triggered automatically, in an event-controlled manner, or in a person-controlled manner (e.g., by the patient or physician). A person-controlled triggering of a data transmission can take place, for example, in a particularly simple manner by placing a magnet or other suitable handheld device onto a body site above the location of the implant to transmit a trigger pulse to the implant 100, with the pulse activating the communication module 40. A telemetry connection 70 can then transmit the pulse transit time Δt or evaluation results to the receiving unit 200. Event-controlled triggering could take place, for example, when a threshold value for the pulse transit time and/or for one of the evaluation results is exceeded.

An analysis, such as in the service center, can then be carried out automatically, and in the process critical conditions, deterioration of the health condition and the like can be diagnosed and visualized. In this way, the physician can capture individual patient values particularly effectively and view additional details, such as in the form of prepared screens. A physician or another person, for example, could access the memory unit 300 of the monitoring system 1000 via an external network, such as an Internet network or a mobile network, as mentioned above.

The pulse transit time Δt and other evaluation results are preferably presented in a form that includes current and historical data and extracted/derived characteristics, with these representing a comprehensive picture of the patient's current health condition and/or the change thereof over time. Different data and characteristics are preferably selectable as desired, and sortable and displayable in different ranges and over different periods. For example, long-term changes, such as over several months, can illustrate age-related changes in arterial compliance. Short-term changes over a day or so can be attributed to physiological blood pressure fluctuations, such as a day-night rhythm, stress and the like. Medium-term changes, which can extend over several days up to several months, allow visualization of the development of a disease or the effect of a therapy. In this way, for example, blood pressure changes can illustrate the impact of diet and/or training Likewise, changes in arterial compliance due to diabetes, development of chronic high blood pressure, and/or pharmaceutical drug effects, can be represented.

The monitoring system 1000 allows primarily diagnostic assessments of patient status, such as the patient's vascular condition and blood pressure, to be made based on the pulse transit time Δt, while taking further evaluation results into consideration. Thus, patient conditions, such as cardiovascular condition, can be readily available. Standard evaluations can be provided, such as daily blood pressure monitoring values including daily mean values, daily minimal values, and daily maximal values for blood pressure. Further evaluation of short-term changes in the pulse transit time Δt, e.g., within the course of a day, and associated representation of blood pressure changes, can provide further diagnostic possibilities. A histogram or other representation of a day-night rhythm of the blood pressure, in particular one which includes an amplitude phase or a 24-hour trend, is useful. Advantageously, a connection between the blood pressure and heart rate can be represented, or a connection between the blood pressure and patient stress. Patient stress can be determined, for example, by way of an acceleration sensor which is additionally accommodated in the implant 100. Blood pressure variability, which can be determined from a frequency analysis of impedance signals, can also be useful. Furthermore, baroreflex sensitivity or latency can be determined as part of further patient values. These quantities can be at least partially derived from the connection between the dynamic blood pressure and changes in the heart rate.

The implant 100, which (as noted above) is preferably designed as a pure monitoring implant, can also be configured as a therapy implant, such as a CRM (Cardiac Rhythm Management) implant, pacemaker, or defibrillator.

Referring to FIGS. 2-6, these primarily relate to the capturing of the first measurement signal S1 associated with the cardiac blood flow B1 at a time $t_{sys}$ at which blood is ejected from the heart, and to the capturing of a second measurement signal S2 associated with the epithoracic peripheral blood flow B2 at a time $t_{gef}$ of a blood pulse in the thoracic tissue. FIG. 2 shows a first preferred version of an implant 100 in the form of a monitoring implant for monitoring a cardiac blood flow B1 and an epithoracic peripheral blood flow B2.

The detector 10 is designed to capture a first measurement signal S1 associated with the blood flow B1 and a second measurement signal S2 associated with the blood flow B2. For this purpose, the detector 10 includes an impedance measuring unit 12, which is connected to an electrode assembly 11.

The impedance measuring unit 12 includes a frequency module 13 connected to the electrodes 11.1 and 11.2. The frequency module 13 includes an exciter module 13.1 for emitting an electric current by way of the electrodes 11.1, 11.2, and a sampling module 13.2 for sampling a voltage by way of the electrodes 11.1, 11.2. The impedance measurement for the second measurement signal S2 is thus implemented by way of the frequency module 13 of the impedance measuring unit 12 employing a two-pole measurement, wherein the voltage sampling is carried by the same electrodes 11.1, 11.2 as those used to supply current into the surrounding tissue. For this purpose, the electrodes 11.1 and 11.2 are situated close to the implant 100 in the form of the housing container 52 and a stump electrode 11.2. The impedance of the second measurement signal S2 is generated by emitting current at a second excitation frequency, which is comparatively low—for example, 2 kHz—and reflects a time-varying impedance curve which captures the circulation in the tissue surrounding the implant. The sampling module 13.2 includes an appropriate low-pass frequency filter, which is able to filter the impedance signal having the lower frequency out of the signal captured by the electrodes 11.1, 11.2. In addition, the frequency module 13 is designed to generate a background signal resulting in a high-frequency background impedance signal, e.g., at 1 MHz, which is measured along with the low-frequency (e.g., 2 kHz) impedance signal. Varying the frequency of the impedance measurement results in a changed contrast between the blood and tissue. Blood has a higher conductivity than tissue, but this discrepancy decreases as the frequency increases. Thus, a higher contrast exists between blood and tissue at lower frequencies (e.g., 2 kHz) than at high frequencies (e.g., 1 MHz). This principle can be used to better separate purely geometric changes—such as potential positional shifts of the electrodes 11.1, 11.2, arm movements, vibrations due to walking, thorax movements, or due to respiration or the like—from the volume pulse of the surrounding blood vessels. The low-frequency impedance signal and the high-frequency background impedance signal are measured by way of the frequency module 13 and the electrodes 11.1, 11.2, and the difference thereof is evaluated. Since geometric changes are considered in the low-frequency impedance measurement signal and the high-frequency background impedance signal equally, while a blood pulse in the thoracic tissue has a higher weighting in the low-frequency impedance signal, the influence of geometric changes can be identified and suppressed.

The frequency module 14, which is connected to the electrodes 11.3, 11.4, functions in a similar fashion, but preferably at an excitation frequency higher than the aforementioned low frequency (and preferably between the aforementioned low and high frequencies), e.g., at 20 kHz. The frequency module 14 includes an exciter module 14.1 and a sampling module 14.2 for emitting a current and sampling a voltage by way of the electrodes 11.3, 11.4. The impedance is then measured at the higher excitation frequency (e.g., 20 kHz) by way of the frequency module 14 and the electrodes 11.3, 11.4 situated away from the implant 100. The first measurement signal S1 is then detected as a time-varying impedance curve, which is indicative of a time at which blood is ejected from the heart, i.e., the signal S1 is associated with the cardiac blood flow B1. By using a higher frequency (e.g., 20 kHz) compared to the aforementioned lower frequency (e.g., 2 kHz), it is better ensured that the first measurement signal S1 captures volume changes of the heart. The frequency module 14 can also determine a high-frequency background impedance signal (e.g., at 1 MHz), as with the frequency module 13 used to determine the second measurement signal S2, and here the lower-frequency (e.g., 20 kHz) impedance signal and the high-frequency (e.g., 1 MHz) background impedance measurement signal separates geometric changes in the electrode position from volume changes of the heart. Geometric changes are substantially equally weighted in both measurements, but the volume change of the heart has a higher weighting in the measurement at the lower frequency of 20 kHz.

The impedance measuring unit 12 furthermore includes a clock pulse module 15, which is designed to alternate the first measurement signal S1 and the second measurement signal S2 together with the associated high-frequency background impedance measurement signals. In other words, the measurements for the first measurement signal S1 (e.g., at 20 kHz) compared to the first background impedance measurement signal, and for the second measurement signal S2 compared to the second background impedance measurement signal, are alternated. As a result, first and second measurement signals S1, S2 are produced, whereby the monitoring assembly 20 connected to the detector 10 is able to generate a first parameter P1 indicative of a time at which blood is ejected from the heart, and a second parameter P2 indicative of a time of a blood pulse in the thoracic tissue.

Figure 3A:
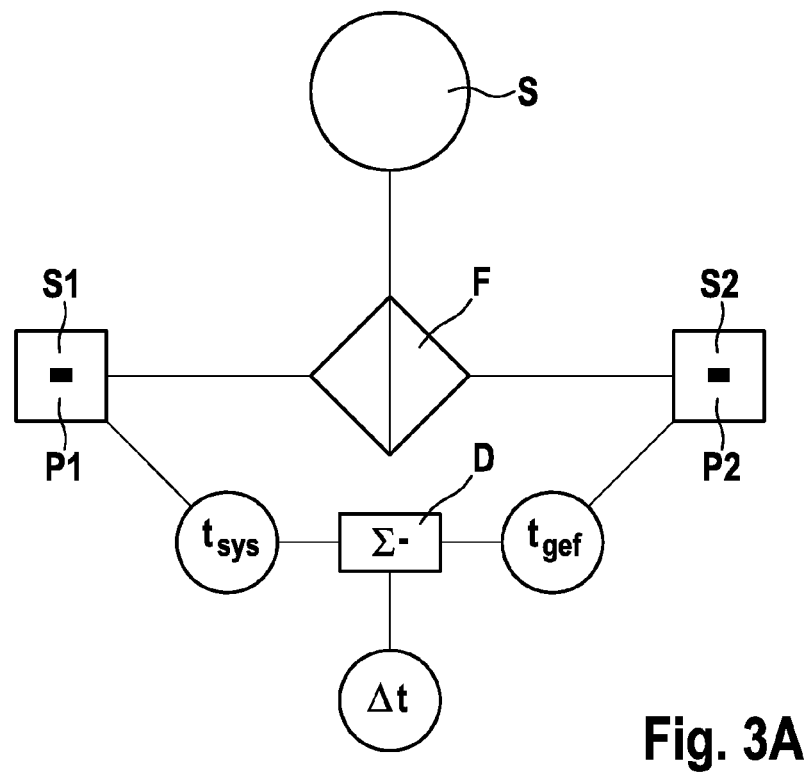
FIGS. 3A, 3B conceptually illustrate frequency-based and amplitude-based alternatives for the use and evaluation of impedance signals in the electromedical implant of FIG. 2.

This frequency-based impedance measuring method for determining the first and second measurement signals S1, S2 at different frequencies is symbolically illustrated in FIG. 3A. In practice, an impedance measurement signal S having oscillating frequency is divided into two signal fractions S1, S2 by a frequency filter F included in the impedance measuring unit 12, and implemented in the frequency module 13, 14. Of these, the first measurement signal S1, which is at a comparatively high frequency, e.g., 20 kHz in the foregoing example, and which is representative of cardiac blood flow, generates the first parameter P1 indicative of a time $t_{sys}$. The second measurement S2, which is at a comparatively lower frequency, e.g., 2 kHz in the foregoing example, and which is representative of a time of a blood pulse in the thoracic peripheral tissue, generates the second parameter P2 indicative of a time $t_{gef}$. The times $t_{sys}$, $t_{gef}$ produced from the parameters P1, P2 are subtracted from each other in a subtractor D, thereby forming the pulse transit time $\Delta t$ ($\Delta t = t_{gef} - t_{sys}$).

Figure 3B:
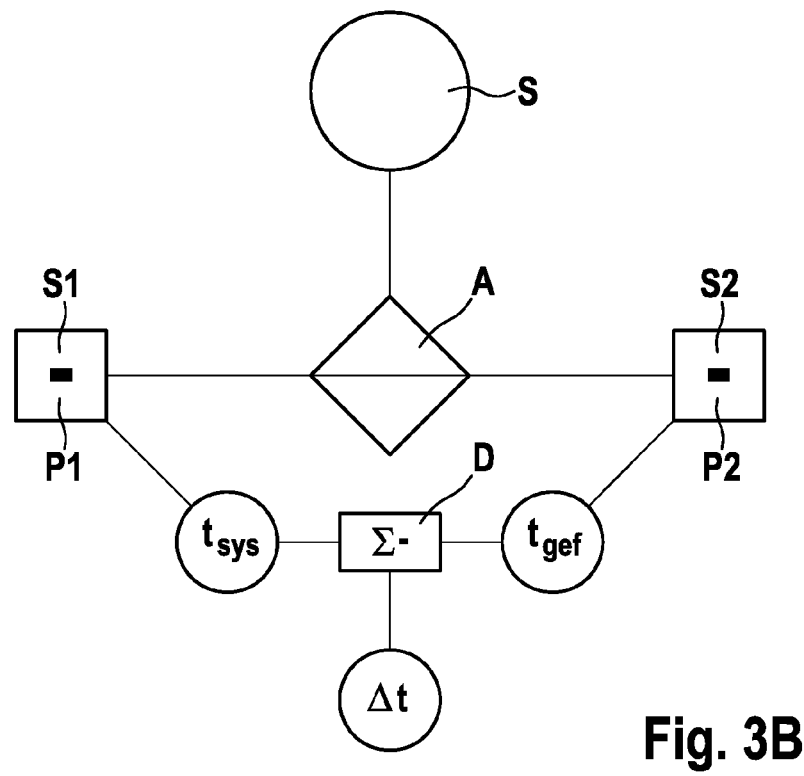

In an alternative version of the invention illustrated in FIG. 3B, the first and second parameters P1, P2 can be obtained from a temporally varying impedance signal S which is separated into a first measurement signal S1 and a second measurement signal S2 on the basis of an amplitude threshold set in an amplitude filter A. The first measurement signal S1 is associated with the cardiac blood flow B1 and the second measurement signal S2 is associated with the epithoracic peripheral blood flow B2. Again, the first parameter P1 can be obtained from the first measurement signal S1 and the second parameter P2 can be obtained from the second measurement signal S2. The time $t_{sys}$ at which blood is ejected from the heart and the time $t_{gef}$ of a blood pulse in the thoracic tissue can be determined from the first and second parameters P1, P2 using a suitable (and known) signal evaluation algorithm, so that again the pulse transit time $\Delta t$ (as the difference between the times $t_{sys}$ and $t_{gef}$) can be determined by way of a subtractor D.

The aforementioned measurement signals S1, S2 should be understood as representing the impedance measurement signals corrected by way of the high-frequency background impedance signal discussed above.

Further elimination of background signals for the first and second measurement signals can be achieved by using signal fractions associated with additional different frequency ranges, associated with elimination of other background effects, wherein these ranges differ from the measurement frequency ranges for the second signal (e.g., 2 kHz) and for the first measurement signal (20 kHz). This can be done, for example, by suitable signal averaging and/or by movement-synchronous signal processing. For example, comparatively high-frequency signal fractions can advantageously be averaged as compared to the measurement frequencies of 2 kHz and 20 kHz. Breathing-synchronous signal fractions or other comparatively low-frequency signal fractions can be eliminated, for example, by synchronous signal processing.

Figure 4:
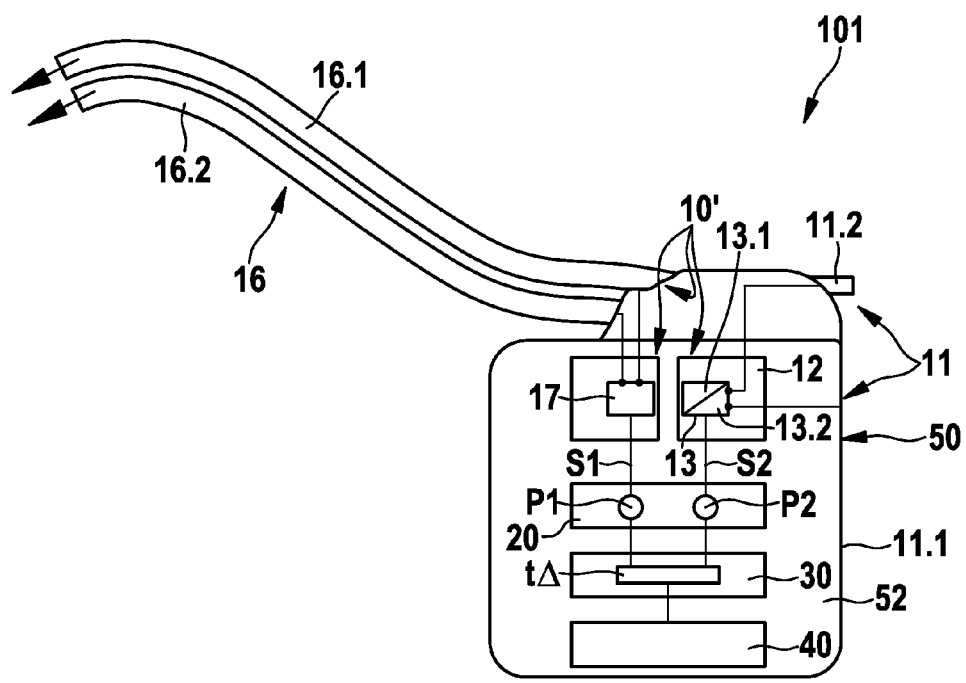
FIG. 4 is a schematic view of an exemplary monitoring implant wherein the first measurement signal is formed as an ECG signal.
Figure 5:
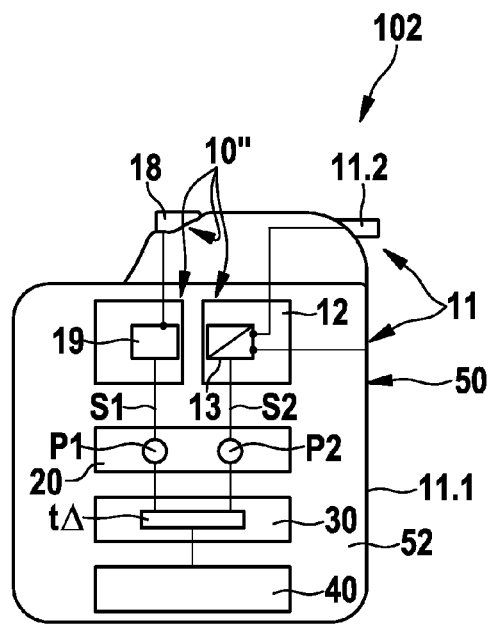
FIG. 5 is a schematic view of an exemplary monitoring implant, wherein the first measurement signal is formed as an acoustic signal.
Figure 6:
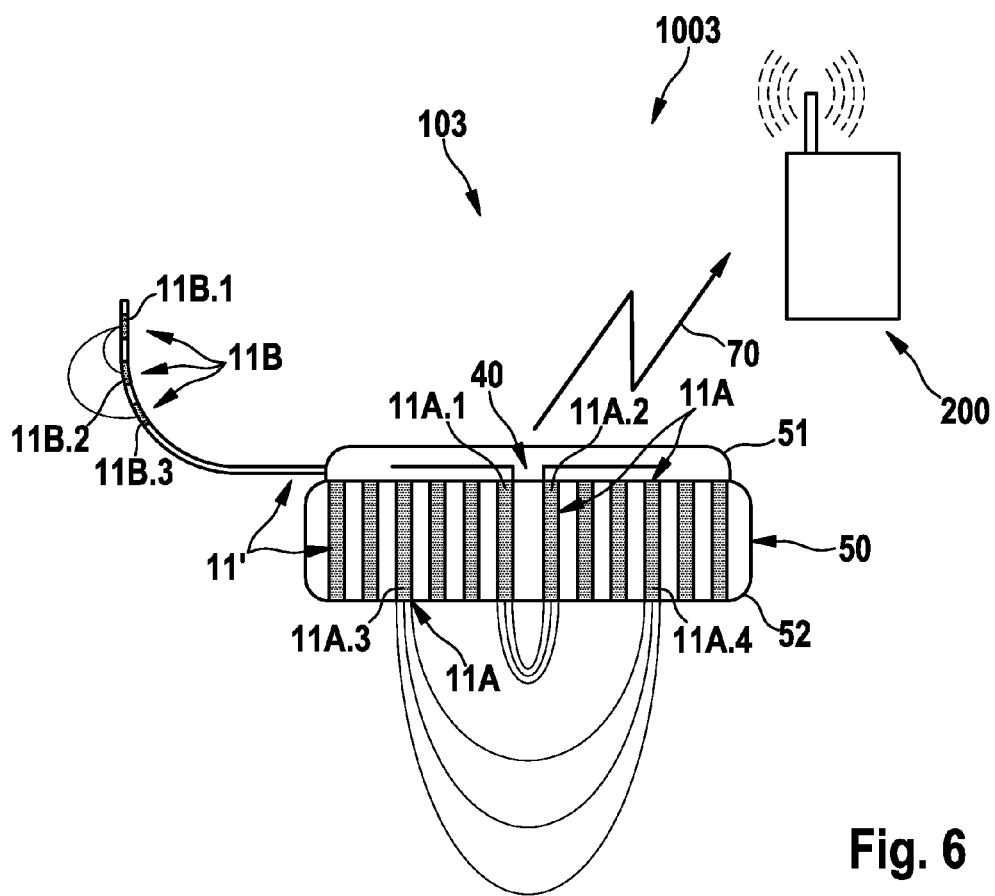
FIG. 6 is a schematic view of an exemplary monitoring implant having an electrode assembly different from that of FIGS. 1, 2, and 4.

Referring next to FIGS. 4-6, measures for determination of the second measurement signal S2 will now be discussed.

FIG. 4 shows a second preferred version of an electromedical implant 101, in which the second measurement signal S2 is determined in a manner resembling that of FIGS. 2 and 3A, and having greater difference from FIG. 3B. The first measurement signal S1 generated by the implant 101 in FIG. 4 is determined as an ECG signal (electrocardiogram signal). For this purpose, the detector 10' includes not only the impedance measuring electrodes 11.1, 11.2 of the electrode assembly 11, but a further electrode assembly 16 including electrodes 16.1, 16.2 and an ECG measuring unit 17, which is connected to the ECG electrodes 16.1, 16.2. The R-wave of the QRS complex in the ECG signal is used as the first parameter P1 which is indicative of a time $t_{sys}$ at which blood is ejected from the heart. By subtracting $t_{sys}$ and the time $t_{gef}$ of a blood pulse in the thoracic tissue (with $t_{gef}$ being determined from the second parameter P2 of the second measurement signal S2), the monitoring assembly 20 and the evaluation unit 30 can determine the pulse transit time $\Delta t$. The pulse transit time $\Delta t$ is transmitted to the communication module 40, which can communicate the pulse transit time $\Delta t$ to a receiving unit 200 of the monitoring system 1000 of FIG. 1.

The principles of the versions shown in FIGS. 2 and 4, as well as in FIGS. 5 and 6, do not necessarily have to be implemented as alternatives, and can also be combined with each other. To illustrate, the first parameter P1 (or the time $t_{sys}$ at which blood is ejected from the heart) can be determined based on an ECG signal according to FIG. 4, and also based on a cardiac impedance signal according to FIG. 2. Thus, an electromedical implant could include the ECG measuring unit 17 of the implant 101, in addition to the impedance measuring unit 12 of the implant 100.

FIG. 5 shows another version of an electromedical implant 102 wherein the detector 10″ has an impedance measuring unit 12 including an electrode assembly 11 bearing the electrodes 11.1 and 11.2. The detector 10″ is configured to detect the second measurement signal S2 in the form of an impedance signal. With respect to the second parameter P2 and the time $t_{gef}$, reference is made to the foregoing description relating to the impedance measuring unit 12 and the frequency module 13 of FIG. 2. Here the time $t_{sys}$ of a blood ejection from the heart is derived from a first parameter P1 of the first measurement signal S1, wherein the first measurement signal S1 is transmitted by an acoustic sensor 18 to an acoustic measuring unit 19, whereby these components are together able to detect cardiac sounds and determine valve closing times of the heart 1. In an alternative version of the implant 102, which is not shown here, the sensor 18 could be designed as an acceleration sensor which is able to directly detect the ventricular blood ejection. As with the implants described above, the evaluation unit 30 determines the pulse transit time $\Delta t$ from $t_{sys}$ (derived from the first parameter P1) and $t_{gef}$ (derived from the second parameter P2), with these quantities being obtained by the monitoring assembly 20, and the pulse transit time $\Delta t$ is ultimately transmitted to the communication module 40.

In all versions mentioned above, additional components for signal processing can be provided in order to generate a first measurement signal S1 and a second measurement signal S2 having minimal possible interference, and being limited to the cardiac blood flow or epithoracic peripheral blood flow. Additional interference, or time intervals having unreliable data, can be identified either by using additional detectors or by way of known error detection algorithms, and can be taken into consideration when forming and/or evaluating the first and second measurement signals S1, S2. An accelerator sensor has proven particularly useful for this purpose by capturing measurement signals only during a resting period of the patient. Such measurement signals can be particularly free of interference because respiratory movements or other patient thorax movements have comparatively low amplitudes. As an alternative or additional approach, advantageous measures include completely discarding signal intervals rendered unusable due to interference.

In order to suppress noise and minor interference in all measurement signal fractions, suitable filtration and averaging measures can be provided. It can be useful to average time values, in particular time differences of the pulse transit time $\Delta t$, over a number of cardiac cycles in order to smooth a transient course of the pulse transit time $\Delta t$.

In addition, first order or higher derivations and other parameter calculations can be useful for determining trends and/or trend parameters, or capture them with greater precision as signal fractions.

Physiological interference is typically subject to a certain rhythm, such as respiration. By using suitable averaging or filtration, as described above, or also by triggering for certain respiratory phases, the effects of respiratory movements or other movements can be suppressed, in particular by using an acceleration sensor.

Special circumstances, such as arrhythmia, a high heart rate or also extrasystoles, can additionally be extracted and removed from a measurement signal by special signal detection measures.

FIG. 6 shows another preferred version of an electromedical implant having a particularly preferred alternative electrode assembly 11′. A monitoring system 1003 modified from that of FIG. 1 includes a modified electromedical implant 103 having an inner design similar to that of the electromedical implant 100. Again, a housing 50 having a housing container 52, a header 51, and an electrode assembly 11′ is provided. By way of a communication module 40 situated in the header 51, the electromedical implant 103 can establish a wireless telemetry connection 70 to a receiving unit 200 of the monitoring system 1003. An antenna, such as an RF antenna or another telemetry connection which does not unduly affect the patient, is used as the telemetry unit in the communication module. Otherwise, the discussion above regarding FIG. 1 generally applies to the monitoring system 1003. The electrode assembly 11′ includes electrodes 11A situated close to the housing 50 and electrodes 11B situated away on a lead. The electrodes 11A are attached as strip electrodes isolated from the housing container 52, which does not serve as an electrode. The electrodes 11A close to the housing 50, together with the impedance measuring unit (not shown in FIG. 6), are used to determine the second measurement signal S2, which is associated with an epithoracic peripheral blood flow B2. The electrodes 11B away from the implant, together with the impedance measuring unit, are used to determine a first measurement signal S1, which is associated with a cardiac blood flow B1. The discussion above regarding the electrodes 11.1 and 11.2 in FIG. 2 generally applies to the electrodes 11A, and the discussion above regarding the electrodes 11.3 and 11.4 in FIG. 2 generally applies to the electrodes 11B. An impedance measurement signal S, i.e., the first measurement signal S1 and the second measurement signal S2 determined at different frequencies, can again be determined using frequency modules (similar to the frequency modules 13, 14 in FIG. 2) in the impedance measuring unit.

In FIG. 6, the electrodes 11A are configured as strip electrodes. In an alternative version not shown in the drawings, the electrodes 11A can be configured as annular electrodes. Annular electrodes are strip-shaped electrodes which run around the entire housing container 52 to encircle the entirety of its circumference. Strip electrodes in FIG. 6 are situated only on one side or on two opposing sides of the housing container 52, without mutually opposing or adjacent strip electrodes contacting each other. However, through suitable connections of the strip electrodes 11A, pairs of strip electrodes—such as a pair of strip electrodes 11A.1 and 11A2—can be coupled for the purpose of a two-pole measurement in order to utilize a current for measuring a thoracic conductivity at a comparatively low frequency (e.g., at 2 kHz). Since the pair of electrodes 11A.1 and 11A.2 is located comparatively close to each other, the range of influence of the expressed current (or of the detected voltage) has comparatively small dimensions in the surrounding tissue of the implant 103. In contrast, a more widely spaced set of electrodes 11A.3 and 11A.4 can capture a range of influence of the surrounding tissue having comparatively large dimensions. Further electrodes can be combined in pairs having varied distances. In this way, different measuring configurations can be created and used by the impedance measuring unit in combination, or in alternating fashion, to obtain impedance signals having different informational content, and/or having different ranges of influence within the tissue. This may prove useful if, for example, the second parameter P2 (representing the time of a blood pulse in the thoracic tissue) is to be redundantly determined from several second measurement signals S2. Analogously, electrodes that differ from the electrodes 11B, such as the electrodes 11B.1 and the electrodes 11B.2, can be connected in pairs in order to capture a narrow distal cardiac impedance curve for the first measurement signal S2. As an alternative, the three distal electrodes 11B.1, 11B.2, 11B.3 can also be used for capturing ECG and related signals. Thus, the design of the electrode assembly 11 in the implant 103 of FIG. 6, or electrode arrangements utilizing similar concepts, allow the capture of impedance signals from different ranges of influence—i.e., having smaller or larger dimensions in the tissue—by coupling electrodes at different locations into pole pairs.

The foregoing example assumes a two-pole measurement wherein voltage measurement and current emission are carried out by the same electrodes. In principle, it is possible to conduct measurements such that the electrode(s) used for voltage sampling differ, at least in part, from the electrode(s) used for current emission.

To briefly summarize the electromedical implants 100, 101, 102, 103 of FIGS. 1-2, 4, and 6—which, again, merely represent examples of the forms the invention may take—the implants monitor a cardiac blood flow B1 and an epithoracic, peripheral blood flow B2 of a living being, and include:

A detector 10, 10', 10" configured to capture a first measurement signal S1 associated with the cardiac blood flow B1, and a second measurement signal S2 associated with the epithoracic, peripheral blood flow B2. The detector 10, 10', 10" includes an impedance measuring unit 12 having an electrode assembly 11, 11', and is preferably configured to detect at least the second measurement signal S2 in the form of an impedance signal.

A monitoring assembly 20 in communication with the detector 10, 10', 10', and which is configured:
(1) to generate a first parameter P1 from the first measurement signal S1 which is indicative of a time $t_{sys}$ at which blood is ejected from the heart, and
(2) to generate a second parameter P2 from the second measurement signal S2 which is indicative of a time $t_{gef}$ of a blood pulse in the thoracic tissue, and which is associated with the ejection of blood.

An evaluation unit 30 in communication with the monitoring assembly 20, and which is configured to generate a pulse transit time $\Delta t = t_{gef} - t_{sys}$ from the first parameter P1 and the second parameter P2.

It is emphasized that the foregoing description and drawings relate to exemplary versions of the invention, which is not intended to be limited to these versions, but rather is intended to be limited only by the claims set out below. Thus, the invention encompasses all different versions that fall literally or equivalently within the scope of these claims.

What is claimed is:

1. An electromedical implant including:
 a. a detector configured to obtain:
  (1) a first measurement signal (S1) associated with a cardiac blood flow (B1) of a living being, and
  (2) a second measurement signal (S2) associated with an epithoracic, peripheral blood flow (B2) of the living being, the second measurement signal (S2) being an impedance signal;
 b. a monitoring assembly in communication with the detector, the monitoring assembly being configured to obtain:
  (1) a first parameter (P1) from the first measurement signal (S1) representative of a time ($t_{sys}$) at which blood is ejected from the heart, and
  (2) a second parameter (P2) from the second measurement signal (S2) representative of a time ($t_{gef}$) of a blood pulse in the thoracic tissue which is associated with the ejection of blood;
 c. an evaluation unit in communication with the monitoring assembly, the evaluation unit being configured to generate a pulse transit time ($\Delta t$) from the first parameter (P1) and the second parameter (P2).

2. The implant of claim 1 wherein the first measurement signal (S1) is an impedance signal (S).

3. The implant of claim 1 wherein the first measurement signal (S1) is an ECG (electrocardiogram) signal.

4. The implant of claim 1 wherein the detector includes:
 a. an impedance measuring unit configured to determine impedance, and
 b. an electrode assembly in communication with the impedance measuring unit.

5. The implant of claim 4 wherein the electrode assembly includes several poles whereby several impedance signals (S) can be determined by the impedance measuring unit.

6. The implant of claim 4 wherein the impedance measuring unit includes:
 a. an exciter module for delivering an electric current via the electrode assembly, and
 b. a sampling module for receiving a voltage via the electrode assembly.

7. The implant of claim 1 wherein the detector includes an electrode assembly, the electrode assembly including at least one electrode defined on a housing container defined about the implant.

8. The implant of claim 1 wherein the detector includes an electrode assembly, the electrode assembly including at least one electrode extending about the entirety of the circumference of a housing container defined about the implant.

9. The implant of claim 1 wherein the first measurement signal (S1) and the second measurement signal (S2) are obtained at different frequencies.

10. The implant of claim 1 wherein the second measurement signal (S2) is obtained at a frequency lower than any frequency at which the first measurement signal (S1) is determined.

11. The implant of claim 1 wherein the detector unit is configured to obtain the first measurement signal (S1) and the second measurement signal (S2) at different times.

12. The implant of claim 1 wherein the detector unit is configured to obtain a background impedance measurement signal at a frequency higher than any frequency at which the first measurement signal (S1) and second measurement signal (S2) are obtained.

13. The implant of claim 1 wherein the first measurement signal (S1) and the second measurement signal (S2) are defined by a portions of a time-varying impedance measurement signal (S) on opposite sides of an amplitude threshold.

14. The implant of claim 1 wherein the detector includes one or more of:
 a. an acoustic detector,
 b. an optical detector,
 c. a pressure and/or expansion detector, and
 d. an acceleration detector.

15. The implant of claim 1 further including a communication module for the wireless transmission of one or more of:
 a. the pulse transit time ($\Delta t$), and
 b. an evaluation result generated from the pulse transit time ($\Delta t$) by the evaluation unit.

16. The implant of claim 15 further including:
 a. a receiving unit remote from the implant, the receiving unit being configured to wirelessly receive one or more of:
  (1) the pulse transit time ($\Delta t$), and
  (2) the evaluation result generated from the pulse transit time ($\Delta t$) by the evaluation unit;

b. a memory configured to store one or more of the pulse transit time (Δt) and the evaluation result.

17. A method for determining the pulse transit time (Δt) within a living being, the method including the performance of the following steps within an implant situated within a living being:
   a. detecting a first measurement signal (S1) associated with the cardiac blood flow (B1) of the living being;
   b. detecting a second measurement signal (S2) associated with the epithoracic, peripheral blood flow (B2) of the living being, the second measurement signal (S2) being an impedance signal;
   c. determining a first parameter (P1) from the first measurement signal (S1), wherein the first parameter (P1) is representative of a time ($t_{sys}$) at which blood is ejected from the heart;
   d. determining a second parameter (P2) from the second measurement signal (S2), the second parameter (P2) being representative of a time ($t_{gef}$) of a blood pulse in the thoracic tissue which is associated with the ejection of blood;
   e. determining a pulse transit time (Δt) from the first parameter (P1) and the second parameter (P2).

18. The method of claim 17 wherein the first measurement signal (S1) is one or more of:
   a. an impedance signal (S), and
   b. an ECG (electrocardiogram) signal.

19. The method of claim 17 wherein the first measurement signal (S1) and the second measurement signal (S2) are obtained at different frequencies.

20. The method of claim 17 wherein the second measurement signal (S2) is obtained at a frequency lower than any frequency at which the first measurement signal (S1) is determined.

21. The method of claim 17 wherein the first measurement signal (S1) and the second measurement signal (S2) are obtained at different times.

22. The method of claim 17 further including the steps of:
   a. detecting a background impedance measurement signal at a frequency higher than any frequency at which the first measurement signal (S1) and second measurement signal (S2) are obtained, and
   b. determining the pulse transit time (Δt) in dependence on the first measurement signal (S1), second measurement signal (S2), and the background impedance measurement signal.

23. The method of claim 17 further including the step of wirelessly transmitting one or more of:
   a. the pulse transit time (Δt), and
   b. the evaluation result generated from the pulse transit time (Δt) by the evaluation unit;
to a receiving unit situated remotely from the living body.

* * * * *